United States Patent [19]

Gastrock et al.

[11] Patent Number: 4,719,303

[45] Date of Patent: Jan. 12, 1988

[54] PREPARATION OF SUBSTITUTED AND UNSUBSTITUTED 2-[(1-CARBAMOYL-1,2-DIMETHYL-PROPYL)-CARBAMOYL]-3-QUINOLINECARBOXYLIC, NICOTINIC AND BENZOIC ACIDS

[75] Inventors: William H. Gastrock, Vicksburg, Miss.; Timothy F. Mason, Plainsboro; Gregory P. Withers, Lawrenceville, both of N.J.

[73] Assignee: American Cyanamid Company, Stamford, Conn.

[21] Appl. No.: 553,933

[22] Filed: Nov. 21, 1983

[51] Int. Cl.$^4$ .................... C07B 43/06; C07D 213/81; C07C 101/42
[52] U.S. Cl. .................... 546/169; 546/297; 546/299; 546/309; 546/318; 562/443; 564/129; 564/134
[58] Field of Search ............... 546/297, 299, 309, 318, 546/169; 562/443; 564/134, 129

[56] References Cited

U.S. PATENT DOCUMENTS 3,673,198  6/1972  Doyle et al. .................... 546/318
4,405,791  9/1983  Rutter et al. .................... 546/318

OTHER PUBLICATIONS

March, J., "Advanced Organic Chemistry", Second Edition, McGraw-Hill, (1977), pp. 331–333.
Morrison and Boyd, "Organic Chemistry", 3rd Edition, Allyn and Bacon, Inc., (1973), pp. 30–32.
Streitwieser, et al., "Introduction to Organic Chemistry", pp. 433–434, (1976).

*Primary Examiner*—Henry R. Jiles
*Assistant Examiner*—Dale A. Bjorkman
*Attorney, Agent, or Firm*—Estelle J. Tsevdos

[57] ABSTRACT

A method for the preparation of substituted and unsubstituted 2-[(1-carbamoyl-1,2-dimethyl-propyl) carbamoyl]-3-quinolinecarboxylic, nicotinic and benzoic acids.

20 Claims, No Drawings

PREPARATION OF SUBSTITUTED AND UNSUBSTITUTED 2-[(1-CARBAMOYL-1,2-DIMETHYLPROPYL)-CARBAMOYL]-3-QUINOLINECARBOXYLIC, NICOTINIC AND BENZOIC ACIDS

The present invention relates to a method for the preparation of 2-[(1-carbamoyl-1,2-dimethylpropyl)carbamoyl]-3-quinolinecarboxylic, nicotinic and benzoic acids, having the structure indicated below by formula (I):

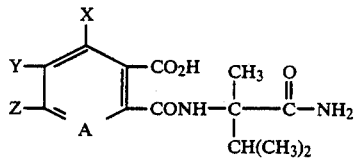

wherein A is N or $CX^1$; X and $X^1$ are each independently hydrogen, halogen, or $C_1$-$C_4$ alkyl; Y is hydrogen, halogen, $C_1$-$C_4$ alkyl, $C_1$-$C_4$ alkoxy, trifluoromethyl, trichloromethyl, difluoromethoxy, diloweralkylamino, $C_1$-$C_4$ alkylthio, phenyl, phenoxy, or phenyl or phenoxy substituted with one $C_1$-$C_4$ alkyl, $C_1$-$C_4$ alkoxy or halogen; Z represents hydrogen, $C_1$-$C_4$ alkyl, trifluoromethyl, trichloromethyl, phenyl or phenyl substituted with one $C_1$-$C_4$ alkyl, $C_1$-$C_4$ alkoxy or halogen; and, when taken together, Y and Z may form a ring in which YZ are represented by the structure, $-(CH_2)_n-$, wherein n is an integer selected from 3 to 5, provided that X is hydrogen; or YZ is

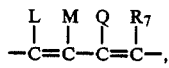

wherein L, M, Q and $R_7$ each represent hydrogen, halogen, $C_1$-$C_4$ alkyl, $C_1$-$C_4$ alkoxy, $C_1$-$C_4$ haloalkyl, difluoromethoxy, diloweralkylamino, $C_1$-$C_4$ alkylthio, nitro, phenyl, phenoxy, or mono-substituted phenyl or phenoxy where the substituent is one $C_1$-$C_4$ alkyl, $C_1$-$C_4$ alkoxy or halogen; with the proviso that only one of L, M, Q or $R_7$, may represent a substituent other than hydrogen, halogen, $C_1$-$C_4$ alkyl or $C_1$-$C_4$ alkoxy. This method comprises reacting a substituted or unsubstituted 2,3-quinolinedicarboxylic, 2,3-pyridinedicarboxylic, or phthalic anhydride as depicted in formula II, with from about 1.0 to about 1.5 molar equivalents of 2-amino-2,3-dimethylbutyronitrile, in the presence of a hydrocarbon or chlorinated solvent containing about 1.0 to 3.0 molar equivalents of a polar aprotic co-solvent. Useful aprotic co-solvents include dimethylsulfoxide, dimethylformamide, acetonitrile, acetone or nitrobenzene, or mixtures thereof.

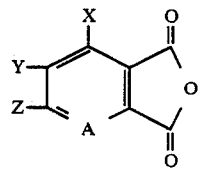

*Wherein Y, Z, X and A are defined as above.

This resultant mixtured is heated at a temperature range of about 25° C. to 60° C., for about one to four hours. Then, the thus-formed formula III compound, 2-[(1-cyano-1,2-dimethylpropyl)carbamoyl]-3-quinolinecarboxylic, nicotinic, or benzoic acid, is hydrolyzed in several ways. Hydrolysis under mild acid conditions is accomplished by the addition of about 1.0 to 1.5 molar equivalents of water in the presence of from 0.10 to 2.0 molar equivalents of sulfuric, hydrochloric, or toluenesulfonic acid, or mixtures thereof, in a hydrocarbon or chlorinated hydrocarbon solvent. Useful hydrocarbon solvents include heptane, toluene, xylene, methylene chloride, chloroform, a dichloroethane, or a trichloroethane in the presence of about 0.0 to 3.0 molar equivalents of a polar aprotic co-solvent such as dimethylsulfoxide, dimethylformamide, acetonitrile, acetone, nitrobenzene, or mixtures thereof. The acid hydrolysis takes place at a temperature range of about 20° C. to 60° C. for a period of about one to five hours.

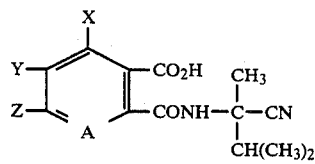

*Wherein Y, Z, X and A are defined above.

Alternatively, hydrolysis can be accomplished under basic conditions with about 2.0 to 5.0 molar equivalents of an alkali metal hydroxide in the presence of about 1.5 to 5.0 molar equivalents of 30% to 70% hydrogen peroxide in a hydrocarbon or chlorinated hydrocarbon solvent. The useful solvents include heptane, toluene, xylene, methylene chloride, chloroform, a dichloroethane, or trichloroethane, or water in combination with about 0.5 to 3.0 molar equivalents of a polar aprotic co-solvent. These co-solvents include dimethylsulfoxide, dimethylformamide, acetonitrile, acetone, or the like. These are reacted at a temperature range of about 20° C. to 60° C. for about one-half to about two hours.

The reaction is preferably conducted in a basic water/DMSO mixture obtained by extracting the formula III acid product and DMSO present in the first stage of the reaction sequence into the aqueous base, and proceeding as described above. Flow Diagram I below graphically illustrates the present reaction sequences:

FLOW DIAGRAM (I)

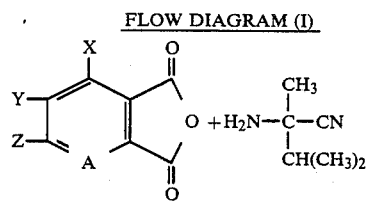

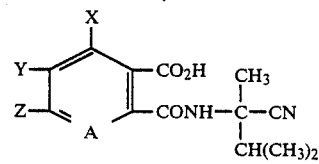

-continued
FLOW DIAGRAM (I)

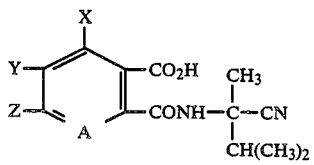

formula (III) compound
1. Aqueous base extraction
2. Hydrogen peroxide
+ water/acid catalyst

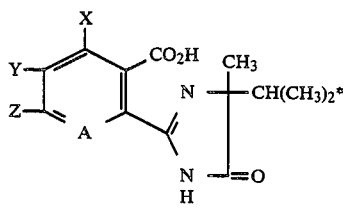

formula (I) compound

The present invention uniquely utilizes hydrocarbon and chlorinated hydrocarbon solvents and water with about 1.0 to 3.0 molar equivalents of a polar aprotic co-solvent. It has been found that particularly when dimethylsulfoxide is used, Formula (I) 2-[(1-carbamoyl-1,2-dimethylpropyl)carbamoyl]-3-quinolinecarboxylic, nicotinic, and benzoic acids yields are enhanced.

Additionally, the catalytic acid hydrolysis employed in this process provides a method for the preparation of formula (I) 2-[(1-carbamoyl-1,2-dimethylpropyl)carbamoyl]-3-quinolinecarboxylic, nicotinic, and benzoic acids in situ by the addition of stoichiometric amounts of water (1.0 to 1.5 molar equivalents) and catalytic amounts of sulfuric, hydrochloric, or p-toluenesulfonic acids (0.10 to 2.0 molar equivalents). When doing so, yields increase to about 90% by utilizing very mild conditions illustrated in Flow Diagram I.

It should be recognized that this catalytic acid hydrolysis can be independently employed in the presence of about 0 to 3.0 molar equivalents of a polar aprotic solvent for the hydrolysis of substituted or unsubstituted formula (III) nitriles illustrated below:

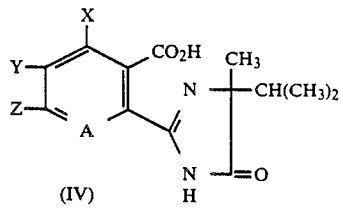

(III)*

*Wherein X, Y, Z and A are as previously defined.

Not only does the present invention enhance yields, but the process of the present invention is of particular importance in the preparation of certain herbicidal imidazolinyl benzoates described in U.S. Pat. No. 4,188,487, and certain herbicidal imidazolinyl nicotinic and 3-quinolinecarboxylic acids described in the co-pending application for U.S. Letters Patent of Marinus Los, Ser. No. 382,041, filed May 25, 1982, now U.S. Pat. No. 4,638,068 represented by formula IV below:

(IV)

*Wherein A, X, Y and Z are as described above.

By directly reacting the formula I substituted or unsubstituted 2-[(1-carbamoyl-1,2-dimethylpropyl)carbamoyl]benzoic, 3-quinolinecarboxylic or nicotinic acid prepared by the method of the present invention with about 2.0 to 20.0 molar equivalents of aqueous sodium or potassium hydroxide at about 25° C. to 100° C. for two to six hours, then, adjusting the pH of the reaction mixture to a pH of about 1.5 to 4.5, the desired formula IV imidazolinyl benzoic, 3-quinolinecarboxylic, and nicotinic acid as illustrated below in Flow Diagram II result:

FLOW DIAGRAM (II)

(I)

Aqueous Base →

(IV)

wherein X, Y, Z and A are as described for formula I.

The present invention increases yields by about 5% to 15% of formula IV herbicidal 2-imidazolin-2-yl 3-quinolinecarboxylic, nicotinic and benzoic acids. In addition to the enhanced yields of final product, the present invention results in fewer undesirable effluents and waste materials.

Additionally, the present reaction system is compatible with each of the reaction sequences, thereby minimizing the need to isolate intermediate compounds and enabling the integration of several process steps.

The present invention is further illustrated by the following examples:

EXAMPLE 1

Integrated process using basic hydrogen peroxide hydrolysis for the presparation of 6-[(1-carbamoyl-1,2-dimethylpropyl)carbamoyl]-m-toluic acid and 2-[(1-carbamoyl-1,2-dimethylpropyl)carbamoyl]-p-toluic acid and conversion to 2-(4-isopropyl-4-methyl-5-oxo-2-imidazolin-2-yl)-p-toluic acid and 6-(4-isopropyl-4-methyl-5-oxo-2-imidazolin-2-yl)-m-toluic acid

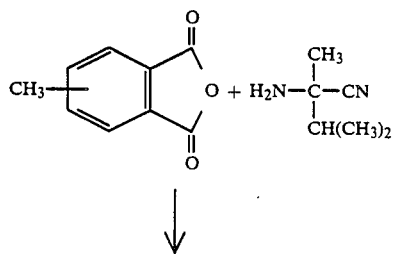

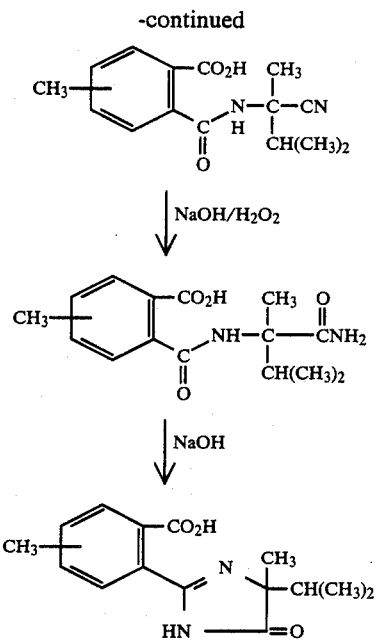

2-Amino-2,3-dimethylbutyronitrile (11.75 g, 0.105 mol) is added to a solution of 4-methylphthalic anhydride (16.20 g, 0.10 mol) in a single solvent or solvent-/co-solvent mixture. The temperature is allowed to increase to about 35° C. to 40° C. This reaction mixture is stirred at a temperature of about 35° C. to 40° C. for two hours and then is cooled to room temperature. The products are extracted from the reaction mixture into water containing sodium hydroxide (14 g, 0.35 mol), and the aqueous phase is then separated from the reaction mixture.

Hydrogen peroxide (45.33 g, 30%, 0.40 mol) is added to the basic solution of 1-(1-cyano-1,2-dimethylpropyl)-4(and 5)-phthalamic acids, and the reaction mixture is stirred at 30° C. for one hour to prepare a mixture of 6-[(1-carbamoyl-1,2-dimethylpropyl)carbamoyl]-m-toluic acid and 2-[(1-carbamoyl-1-dimethylpropyl)carbamoyl]-p-toluic acid.

The reaction mixture is then heated at about 80° C. to 90° C. for two to three hours in order to form the desired mixture of 2-(4-isopropyl-4-methyl-5-oxo-2-imidazolin-2-yl)-p-toluic acid and 6-(4-isopropyl-4-methyl-5-oxo-2-imidazolin-2-yl)-m-toluic acid.

The results of experiments using different solvents and solvent/co-solvent mixtures are summarized in Table I.

TABLE I

Integrated process using basic hydrogen peroxide hydrolysis for the preparation of 6-[(1-carbamoyl-1,2-dimethylpropyl)-carbamoyl]-m-toluic acid and 2-[(1-carbamoyl-1,2-dimethylpropyl)carbamoyl]-p-toluic acid and conversion to 2-(4-isopropyl-4-methyl-5-oxo-2-imidazolin-2-yl)-p-toluic acid and 6-(4-isopropyl-4-methyl-5-oxo-2-imidazolin-2-yl)-m-toluic acid.

| Solvent | Co-Solvent/ Molar Equivalents | Product Yield Percent (%) |
|---|---|---|
| Methylene chloride | None | 74 |
| 1,1,2-Trichloroethane | None | 74 |
| 1,1,2-Trichloroethane | DMSO/1.1 | 92–95 |
| 1,1,2-Trichloroethane | DMF/1.0 | 82 |
| 1,1,1-Trichloroethane | DMSO/1.0 | 88 |
| Methylene chloride | DMSO/1.1 | 93–94 |
| Toluene | DMSO/1.0 | 86 |

It is seen that enhanced yields result when the process is carried out in a solvent/aprotic co-solvent system.

EXAMPLE 2

Preparation of 2-[(1-carbamoyl-1,2-dimethylpropyl)carbamoyl]-3-quinolinecarboxylic acid and conversion to 2-(4-isopropyl-4-methyl-5-oxo-2-imidazolin-2-yl)-3-quinolinecarboxylic acid

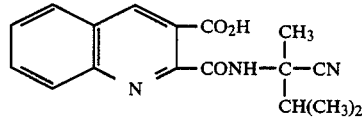

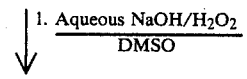

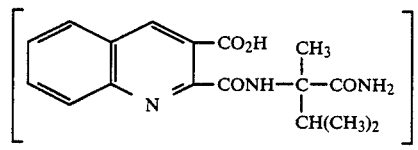

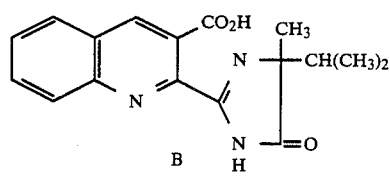

Hydrogen peroxide (30%, 1.25 g, 0.01 mol) is added to two solutions of 2-(1-cyano-1,2-dimethylpropyl)-3-quinolinecarboxylic acid. One solution is an aqueous sodium hydroxide (10 ml H₂O, 0.88 g, 50% NaOH, 0.011 mol) alone, and the other is a solution containing dimethylsulfoxide (0.12 g, 0.0015 mol).

Both reaction mixtures are then heated at 80° C. for three and one-half hours. After cooling each to room temperature, the products of each are isolated by acidification of the reaction mixture and filtration.

The dried isolated products are assayed by High Performance Liquid Chromatography for presence and amount of formula I product and formula III intermediate.

Table II summarizes the results of these experiments.

TABLE II

INTEGRATED PROCESS FOR THE PREPARATION OF 2-(4-ISOPROPYL-4-METHYL-5-OXO-2-IMIDAZOLIN-2-YL)-3-QUINOLINECARBOXYLIC ACID

| Solvent | Co-Solvent/ Molar Equivalent | Yield Percent B** | Yield Percent A* |
|---|---|---|---|
| 4% Aqueous NaOH | None | 52.9 | 55.7 |
| 4% Aqueous NaOH | DMSO/0.5 | 56.0 | 61.9 |

*A = intermediate as defined in Example 2 flow diagram

**B = product as defined in Example 2 flow diagram

EXAMPLE 3

Preparation of N-(1-cyano-1,2-dimethylpropyl)-4(and 5)-methylphthalamic acid

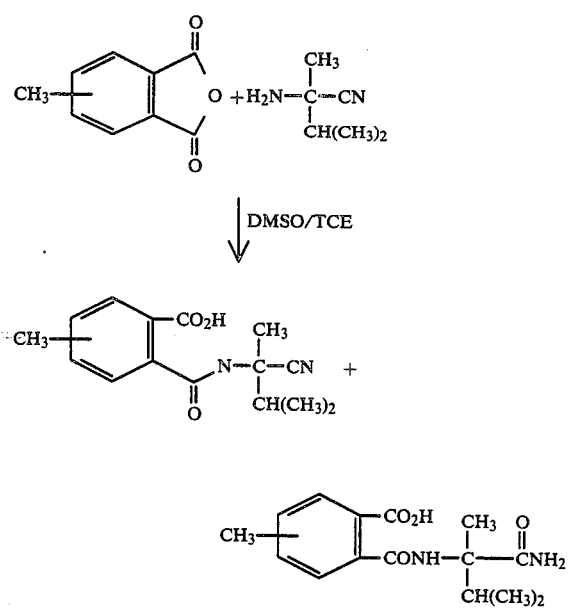

4-Methylphthalic anhydride (16.20 g, 0.10 mol) is dissolved in DMSO (8.60 g 0.11 mol) and 18 ml 1,1,2-trichloroethane. A solution of 2-amino-2,3-dimethylbutyronitrile and 12 ml 1,1,2-trichloroethane is added, allowing the temperature to rise to about 30° C. to 40° C. The resulting mixture is stirred at 35° C. to 40° C. for two hours. Analysis of the reaction mixture by High Performance Liquid Chromatography reveals 90% amidonitrile and 3% diamide.

EXAMPLE 4

Process using catalytic acid hydrolysis for the preparation of 6-[(1-carbamoyl-1,2-dimethylpropyl)carbamoyl]-m-toluic acid and 2-[(1-carbamoyl-1,2-dimethylpropyl)carbamoyl]-p-toluic acid and conversion to 2-(4-isopropyl-4-methyl-5-oxo-2-imidazolin-2-yl)-p-toluic acid and 6-(4-isopropyl-4-methyl-5-oxo-2-imidazolin-2-yl)-m-toluic acid

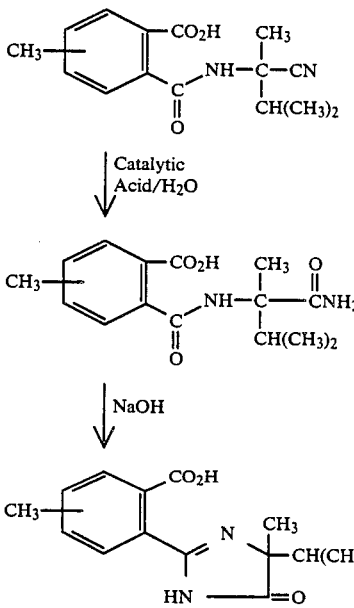

Sulfuric acid (0.98 g, 0.01 mol) and water (1.89 g, 0.105 mol) are added to a solution of amidonitrile (~0.10 mol) in 1,1,2-trichloroethane containing DMSO as described in Example 1. This mixture is maintained at 45° C. to 50° C. for one and one half hours. HPLC analysis shows 95% diamide with no trace of starting material. To this solution is added 50% NaOH (9.68 g, 0.121 mol) and 25 ml H₂O. The phases are separated and the organic phase is washed with 24 ml water. The aqueous layers containing the diamide are combined. Sodium hydroxide (12 g, 0.3 mol) is added to this solution, and it is heated to 80° C. to 85° C. for two hours. Analysis by HPLC shows 95.5% imidazolinyl toluic acids and 1.3% unconverted diamide. The solution is neutralized to pH 8.0 with concentrated sulfuric acid. Methylene chloride or 1,1,2-trichloroethane is added, and the product is extracted into the organic phase at pH 4.0–4.5. The yield of product (based on starting anhydride) is 25.59 g (93.5%).

Utilizing the above procedure and substituting hydrochloric acid (HCl) or p-toluenesulfonic acid (pTSA) for sulfuric acid, 1.0 to 1.2 molar equivalents of water and 0.0 to 3.0 equivalents of polar aprotic co-solvent combination with various solvents affords the desired product in excellent yield, as illustrated in Table III below.

TABLE III

Catalytic acid hydrolisis for the preparation of 6-[1-carbamoyl-1,2-dimethylpropyl)carbamoyl]m-toluic acid and 2-[(1-carbamoyl-1,2-dimethylpropyl)carbamoyl]-p-toluic acid and conversion to 2-(4-isopropyl-4-methyl-5-oxo-2-imidazolin-2-yl)-p-toluic acid and 6-(4-isopropyl-4-methyl-5-oxo-2-imidazolin-2-yl)-m-toluic acid

| Solvent | Co-Solvent | Acid/Molar Equivalents | Yield Percent Cyclized Product |
|---|---|---|---|
| Methylene chloride | DMSO | HCl/0.10 | 94 |
| | | HCl/0.15 | 97 |
| | | HCl/0.30 | 94 |
| Methylene chloride | DMF | HCl/0.10 | 86 |
| Methylene chloride | DMSO | pTSA/0.10 | 97 |
| 1,1,2,2-tetrachloroethylene | DMSO | HCl/0.10 | 92 |
| 1,1,1-trichloroethane | DMSO | HCl/0.10 | 90 |
| 1,2-dichloropropane | DMSO | HCl/0.10 | 86 |
| 1,1,2-trichloroethane | DMSO | HCl/0.10 | 91 |
| Heptane | DMSO | HCl/0.10 | 93 |
| Toluene | DMF | HCl/0.10 | 90 |
| Toluene | Nitrobenzene | HCl/0.10 | 82 |
| Toluene | Acetone | HCl/0.10 | 87 |
| Toluene | Acetonitrile | HCl/0.10 | 86 |
| Toluene | DMSO | HCl/0.15 | 94 |
| Toluene | NONE | HCl/0.15 | 85 |
| Toluene | DMSO | $H_2SO_4$/0.10 | 92 |

EXAMPLE 5

Process using catalytic acid hydrolysis for the preparation of 2-[(1-carbamoyl-1,2-dimethylpropyl)carbamoyl]nicotinic acid and conversion to 2-(4-isopropyl-4-methyl-5-oxo-2-imidazolin-2-yl)nicotinic acid

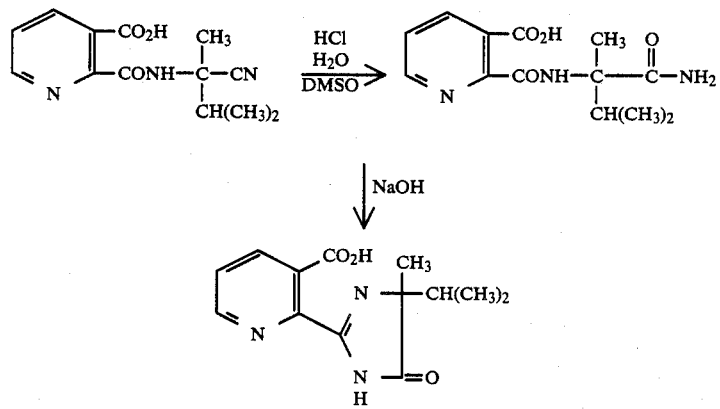

Aqueous hydrochloric acid (37%, 1.5 g, 0.0165 mol) containing water (0.94 g, 0.05 mol) is added to a solution of 1-(1-cyano-1,2-dimethylpropyl)nicotinic acid (8.35 g, 0.053 mol) in toluene (15 ml) containing DMSO (4.7 g, 0.05 mol). The reaction mixture is allowed to stir at 45° C. to 47° C. for a total of six hours. Aqueous sodium hydroxide (34.4 g, 25%, 0.215 mol) is added, and the reaction mixture is then stirred at 65° C. to 70° C. for three hours. The solution is cooled to room temperature; methylene chloride (30 ml) is added; and the mixture is acidified to a pH of 3. The organic phase is separated, and the solvent removed to give an 89.4% yield of 2-(4-isopropyl-4-methyl-5-oxo-2-imidazolin-2-yl)nicotinic acid.

What is claimed is:

1. A method for the preparation of compounds having the structure,

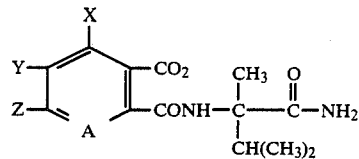

wherein A is N or $CX^1$; X and $X^1$ are each independently hydrogen, halogen, or $C_1$-$C_4$ alkyl, Y is hydrogen, halogen, $C_1$-$C_4$ alkyl, $C_1$-$C_4$ alkoxy, trifluoromethyl, trichloromethyl, difluoromethoxy, diloweralkylamino, $C_1$-$C_4$ alkylthio, phenyl, phenoxy, or phenyl or phenoxy substituted with one $C_1$-$C_4$ alkyl, $C_1$-$C_4$ alkoxy or halogen; Z represents hydrogen, $C_1$-$C_4$ alkyl, trifluoromethyl, trichloromethyl, phenyl or phenyl substituted with one $C_1$-$C_4$ alkyl, $C_1$-$C_4$ alkoxy or halogen; and, when taken together, Y and Z may form a ring in which YZ are represented by the structure, —($CH_2$)$_n$—, where n is an integer selected from 3 to 5, provided that X is hydrogen; or YZ is

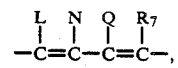

where L, M, Q and $R_7$ each represent hydrogen, halogen, $C_1$-$C_4$ alkyl, $C_1$-$C_4$ alkoxy, $C_1$-$C_4$ haloalkyl, difluoromethoxy, diloweralkylamino, $C_1$-$C_4$ alkylthio, nitro, phenyl, phenoxy, or mono-substituted phenyl or phenoxy where the substitution is one $C_1$-$C_4$ alkyl, $C_1$-$C_4$ alkoxy or halogen; with the proviso that only one of L, M, Q or $R_7$ may represent a substituent other than hydrogen, halogen, $C_1$-$C_4$ alkyl or $C_1$-$C_4$ alkoxy, said method comprising: reacting a compound having the structure,

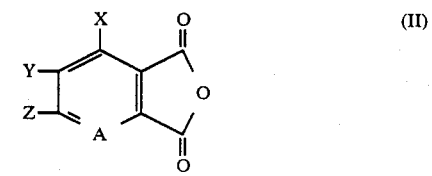

wherein X, Y, Z and A are defined as above, with from about 1.0 to about 1.5 molar equivalents of 2-amino-2,3-dimethylbutyronitrile in the presence of a hydrocarbon or chlorinated hydrocarbon solvent containing 1.0 to 3.0 molar equivalents of the polar aprotic co-solvent dimethylsulfoxide, dimethylformamide, acetonitrile, acetone, nitrobenzene, or mixtures thereof, at a temperature range of about 25° C. to 60° C. for about one to four hours; hydrolyzing the thus-formed compound having the structure,

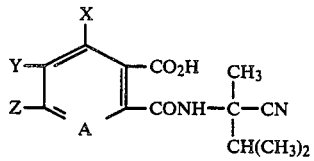
(III)

wherein X, Y, Z and A are as described above, with about 1.0 to 1.5 molar equivalents of water in the presence of catalytic molar equivalents of sulfuric, hydrochloric, toluene sulfonic acid, or mixtures thereof, in a hydrocarbon or chlorinated hydrocarbon solvent in the presence of 1.0 to 3.0 molar equivalents of the polar aprotic co-solvent dimethylsulfoxide, dimethylformamide, acetonitrile, acetone, nitrobenzene, or mixtures thereof, at a temperature range of 20° C. to 60° C., for about one to five hours.

2. A method according to claim 1, wherein said hydrocarbon solvent is heptane, toluene or xylene.

3. A method according to claim 1, wherein said chlorinated hydrocarbon solvent is methylene chloride, chloroform, or dichloroethane or trichloroethane.

4. A method according to claim 1, wherein said formula (I) compounds are 6-[(1-carbamoyl-1,2-dimethylpropyl)carbamoyl]-m-toluic acid and 2-[(1-carbamoyl-1,2-dimethylpropyl)carbamoyl]-p-toluic acid.

5. A method according to claim 2, wherein said polar aprotic co-solvent is 1.0 to 3.0 molar equivalents of dimethylsulfoxide.

6. A method according to claim 2, wherein said formula (I) compounds are 6-[(1-carbamoyl-1,2-dimethylpropyl)carbamoyl]-m-toluic acid and 2-[(1-carbamoyl-1,2-dimethylpropyl)carbamoyl]-p-toluic acid.

7. A method according to claim 3, wherein said polar aprotic co-solvent is 1.0 to 3.0 molar equivalents of dimethylsulfoxide.

8. A method according to claim 3, wherein said formula (I) compounds are 6-[(1-carbamoyl-1,2-dimethylpropyl)carbamoyl]-m-toluic acid and 2-[(1-carbamoyl-1,2-dimethylpropyl)carbamoyl]-p-toluic acid.

9. A method for the preparation of compounds having the structure,

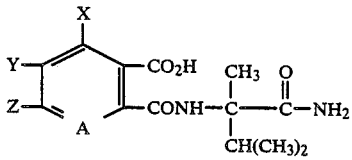
(Ia)

wherein A is N or $CX^1$; X and $X^1$ are each independently hydrogen, halogen or $C_1$-$C_4$ alkyl, Y is hydrogen, halogen, $C_1$-$C_4$ alkyl, $C_1$-$C_4$ alkoxy, trifluoromethyl, trichloromethyl, difluoromethoxy, diloweralkylamino, $C_1$-$C_4$ alkylthio, phenyl, phenoxy, or phenyl or phenoxy substituted with one $C_1$-$C_4$ alkyl, $C_1$-$C_4$ alkoxy or halogen; Z represents hydrogen, $C_1$-$C_4$ alkyl, trifluoromethyl, trichloromethyl, phenyl or phenyl substituted with one $C_1$-$C_4$ alkyl, $C_1$-$C_4$ alkoxy or halogen; and, when taken together, Y and Z may form a ring in which YZ are represented by the structure, $-(CH_2)_n-$, where n is an integer selected from 3 to 5, provided that X is hydrogen; or YZ is

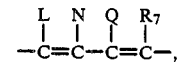

where L, M, Q and $R_7$ each represent hydrogen, halogen, $C_1$-$C_4$ alkyl, $C_1$-$C_4$ alkoxy, $C_1$-$C_4$ haloalkyl, difluoromethoxy, diloweralkylamino, $C_1$-$C_4$ alkylthio, nitro, phenyl, phenoxy, or mono-substituted phenyl or phenoxy where the substituent is one $C_1$-$C_4$ alkyl, $C_1$-$C_4$ alkoxy or halogen; with the proviso that only one of L, M, Q or $R_7$ may represent a substituent other than hydrogen, halogen, $C_1$-$C_4$ alkyl or $C_1$-$C_4$ alkoxy, said method comprising: reacting a compound having the structure,

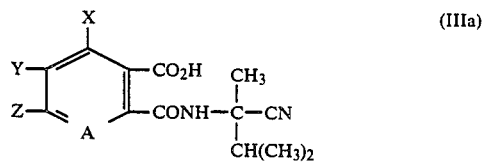
(IIIa)

wherein A, X, Y and Z are as described above with 1.0 to 1.5 molar equivalents of water in the presence of catalytic molar equivalents of sulfuric, hydrochloric, p-toluenesulfonic acid, or mixtures thereof, in a hydrocarbon or chlorinated hydrocarbon solvent in the presence of about 1.0 to 3.0 molar equivalents of the polar aprotic solvent dimethylsulfoxide, dimethylformamide, acetonitrile, acetone, nitrobenzene, or mixtures thereof, at a temperature range of about 20° C. to 60° C. for about one to five hours.

10. A method according to claim 9, wherein said formula (Ia) compounds are 6-[(1-carbamoyl-1,2-dimethylpropyl)carbamoyl]-m-toluic acid and 2-[(1-carbamoyl-1,2-dimethylpropyl)carbamoyl]-p-toluic acid.

11. A method according to claim 9, wherein said formula (Ia) compound is 2-[(1-carbamoyl-1,2-dimethylpropyl)carbamoyl]nicotinic acid.

12. A method according to claim 9, wherein said formula (Ia) compound is 2-[(1-carbamoyl-1,2-dimethylpropyl)carbamoyl]-3-quinolinecarboxylic acid.

13. A method according to claim 9, wherein said hydrocarbon solvent is heptane, toluene or xylene.

14. A method according to claim 9, wherein said chlorinated hydrocarbon solvent is methylene chloride, chloroform, a dichloroethane or trichloroethane.

15. A method according to claim 13, wherein said formula (Ia) compounds are 6-[(1-carbamoyl-1,2-dimethylpropyl)carbamoyl]-m-toluic acid and 2-[(1-carbamoyl-1,2-dimethylpropyl)carbamoyl]-p-toluic acid.

16. A method according to claim 13, wherein said formula (Ia) compound is 2-[(1-carbamoyl-1,2-dimethylpropyl)carbamoyl]nicotinic acid.

17. A method according to claim 13, wherein said formula (Ia) compound is 2-[(1-carbamoyl-1,2-dimethylpropyl)carbamoyl]-3-quinolinecarboxylic acid.

18. A method according to claim 14, wherein said formula (Ia) compounds are 6-[(1-carbamoyl-1,2-dimethylpropyl)carbamoyl]-m-toluic acid and 2-[(1-carbamoyl-1,2-dimethylpropyl)carbamoyl]-p-toluic acid.

19. A method according to claim 14, wherein said formula (Ia) compound is 2-[(1-carbamoyl-1,2-dimethylpropyl)carbamoyl]nicotinic acid.

20. A method according to claim 14, wherein said formula (Ia) compound is 2-[(1-carbamoyl-1,2-dimethylpropyl)carbamoyl]-3-quinolinecarboxylic acid.

* * * * *